(12) United States Patent
Nagaraj et al.

(10) Patent No.: US 11,911,376 B2
(45) Date of Patent: Feb. 27, 2024

(54) METHODS FOR PREVENTING AND TREATING RETINAL DAMAGE

(71) Applicant: THE REGENTS OF THE UNIVERSITY OF COLORADO, Denver, CO (US)

(72) Inventors: Ram H. Nagaraj, Aurora, CO (US); Rooban B. Nahomi, Aurora, CO (US); Mi-hyun Nam, Aurora, CO (US)

(73) Assignee: THE REGENTS OF THE UNIVERSITY OF COLORADO, Denver, CO (US)

( * ) Notice: Subject to any disclaimer, the term of this patent is extended or adjusted under 35 U.S.C. 154(b) by 147 days.

(21) Appl. No.: 17/199,896

(22) Filed: Mar. 12, 2021

(65) Prior Publication Data

US 2021/0299114 A1    Sep. 30, 2021

Related U.S. Application Data

(60) Provisional application No. 63/002,157, filed on Mar. 30, 2020.

(51) Int. Cl.
| | | |
|---|---|---|
| *A61K 31/47* | (2006.01) | |
| *A61P 3/10* | (2006.01) | |
| *A61P 27/06* | (2006.01) | |
| *A61K 9/00* | (2006.01) | |

(52) U.S. Cl.
CPC ............ *A61K 31/47* (2013.01); *A61K 9/0019* (2013.01); *A61K 9/0048* (2013.01); *A61P 3/10* (2018.01); *A61P 27/06* (2018.01)

(58) Field of Classification Search
CPC ............ A61K 31/47; A61P 3/10; A61P 27/06
See application file for complete search history.

(56) References Cited

U.S. PATENT DOCUMENTS

| | | | |
|---|---|---|---|
| 8,183,238 | B2 | 5/2012 | Claffey et al. |
| 8,309,767 | B2 | 11/2012 | Zisapel et al. |
| 8,883,785 | B2 | 11/2014 | Dominguez et al. |
| 9,145,373 | B2 | 9/2015 | Wityak et al. |
| 9,260,422 | B2 | 2/2016 | Dominguez et al. |
| 9,822,058 | B2 | 11/2017 | Toledo-sherman et al. |
| 9,981,918 | B2 | 5/2018 | Toledo-sherman et al. |
| 2005/0118594 | A1 | 6/2005 | Chawla et al. |
| 2008/0287381 | A1 | 11/2008 | Thaler et al. |
| 2018/0354908 | A1 | 12/2018 | Cowley et al. |

FOREIGN PATENT DOCUMENTS

| | | |
|---|---|---|
| WO | 2007002781 A2 | 1/2007 |
| WO | 2017202816 A1 | 11/2017 |
| WO | 2019101641 A1 | 5/2019 |
| WO | 2019101642 A1 | 5/2019 |

OTHER PUBLICATIONS

Nahomi et al., International Journal of Molecular Sciences, 2020, 21, 1795.*
Ana I. Ramirez et al., "The Role of Microglia in Retinal Neurodegeneration: Alzheimer's Disease, Parkinson, and Glaucoma", Frontiers in Aging Neuroscience, 2017, 9(214): 1-21 (21 pages).
Anna Matysik-Wozniak et al., "Effects of tryptophan, kynurenine and kynurenic acid exerted on human reconstructed corneal epithelium in vitro", Pharmacological Reports, 2017, 69: 722-729 (8 pages).
Anna Zinger et al., "The Involvement of Neuroinflammation and Kynurenine Pathway in Parkinson's Disease", Parkinson's Disease, 2011, vol. 2011, 12 pages.
Robert Rejdak et al., "Alterations of kynurenic acid content in the retina in response to retinal ganglion cell damage", Vision Research, 2003, 43: 497-503 (7 pages).
Robert Rejdak et al., "Age-dependent decrease of retinal kynurenate and kynurenine aminotransferases in DBA/2J mice, a model of ocular hypertension", Vision Research, 2004, 44: 655-660 (6 pages).

* cited by examiner

*Primary Examiner* — Sun Jae Yoo
(74) *Attorney, Agent, or Firm* — Dorsey & Whitney LLP

(57) ABSTRACT

Methods of treating, reducing the risk of, preventing, or alleviating at least one symptom of a retinal disease, injury, or condition in a subject involve administering a pharmaceutically effective amount of kynurenic acid to the subject. The kynurenic acid may be administered intravenously or intravitreally. Systems for treating retinal diseases, injuries, or conditions are also disclosed and may include an administration device.

14 Claims, 16 Drawing Sheets

METHODS FOR PREVENTING AND TREATING RETINAL DAMAGE

CROSS REFERENCE TO RELATED APPLICATIONS

The present application claims the benefit of priority to U.S. Provisional Patent Application No. 63/002,157, entitled "METHODS FOR PREVENTING AND TREATING RETINAL DAMAGE," filed Mar. 30, 2020, the entirety of which is hereby incorporated by reference herein for all purposes.

STATEMENT OF GOVERNMENT INTEREST

This invention was made with government support from the National Institutes of Health under grant number P30 DK048520. The government has certain rights in the invention.

TECHNICAL FIELD

The present disclosure relates generally to systems and methods for preventing or treating retinal damage. Specific implementations involve intravenous or intravitreal administration of kynurenic acid to prevent or reduce retinal ganglion cell death caused by injury or disease.

BACKGROUND

Glaucoma affects nearly 60 million people worldwide, and approximately 8 million people are blind from the disease. In the United States, more than 2.9 million people are afflicted with glaucoma, and this number is expected to more than double by 2050. Axonal degeneration and the subsequent death of retinal ganglion cells (RGCs) are the substantial factors causing vision loss in glaucoma patients. RGC death can occur from excitotoxic damage, neuorotrophic factor deprivation, oxidative stress, inflammation, mitochondrial dysfunction and axonal transport failure. Multiple factors thus contribute to RGC death, both individually and especially in combination, making the condition difficult to treat. This problem is exacerbated by a lack of knowledge regarding the precise molecular mechanisms that lead to RGC death, which is also heavily implicated in various ophthalmologic conditions other than glaucoma. Accordingly, methods of effectively combating RGC death are needed.

SUMMARY

Embodiments disclosed herein relate to systems and methods of preventing or treating retinal damage by blocking, slowing and/or reducing RGC death induced by injury or disease.

In accordance with embodiments of the present disclosure, a method of treating, reducing the risk of, preventing, and/or alleviating at least one symptom of a retinal disease, injury, or condition in a subject may involve administering to the subject a therapeutically effective amount of kynurenic acid. In some examples, the kynurenic acid is administered intravenously. In some embodiments, the kynurenic acid is administered at least once within 24 hours after the injury is sustained by the subject or the retinal disease or condition is diagnosed. In some examples, the kynurenic acid is administered at a dose ranging from about 0.05 g per kg of body weight of the subject to about 0.6 g per kg of body weight of the subject. In some embodiments, the kynurenic acid is administered at a dose ranging from about 0.1 g per kg of body weight of the subject to about 0.25 g per kg of body weight of the subject.

In some examples, the kynurenic acid is administered intravitreally. In some embodiments, the kynurenic acid is administered at least once within 24 hours after the injury is sustained by the subject or the retinal disease or condition is diagnosed. In some examples, the kynurenic acid is administered intravitreally at a dose ranging from about 5 mg to about 50 mg. In some embodiments, the kynurenic acid is administered intravitreally at a dose ranging from about 5 mg to about 10 mg.

In some examples, the subject is a human. In some embodiments, the retinal disease, injury, or condition is glaucoma. In some examples, the retinal disease, injury, or condition is selected from the group consisting of: glaucoma, macular degeneration, diabetic eye disease, retinal detachment, and retinitis pigmentosa. In some embodiments, the retinal disease, injury, or condition is caused by excitotoxic damage, physical damage, chemical damage, neurotrophic factor deprivation, oxidative stress, inflammation, mitochondrial dysfunction, axonal transport failure, or combinations thereof. In some examples, the retinal disease, injury, or condition comprises a loss of retinal ganglion cells.

In accordance with embodiments of the present disclosure, a system for treating, reducing the risk of, preventing, and/or alleviating at least one symptom of a retinal disease, injury, or condition in a subject may include an injection device configured to administer to the subject a therapeutically effective amount of kynurenic acid. In some examples, the injection device is an intravenous drip device or a tuberculin syringe. In some embodiments, the retinal disease, injury, or condition is glaucoma. In some examples, the retinal disease, injury, or condition is caused by excitotoxic damage, physical damage, chemical damage, neurotrophic factor deprivation, oxidative stress, inflammation, mitochondrial dysfunction, axonal transport failure, or combinations thereof. In some embodiments, the retinal disease, injury, or condition comprises a loss of retinal ganglion cells. In some examples, the therapeutically effective amount of kynurenic acid ranges from about 0.05 g per kg of body weight of the subject to about 0.6 g per kg of body weight of the subject.

This Summary is neither intended nor should it be construed as being representative of the full extent and scope of the present disclosure. Moreover, references, made herein to "the present disclosure," or aspects thereof, should be understood to mean certain embodiments of the present disclosure and should not necessarily be construed as limiting all embodiments to a particular description. The present disclosure is set forth in various levels of detail in this Summary as well as in the attached drawings and Detailed Description and no limitation as to the scope of the present disclosure is intended by either the inclusion or non-inclusion of elements, components, etc. in this Summary. Features from any of the disclosed embodiments may be used in combination with one another, without limitation. In addition, other features and advantages of the present disclosure will become apparent to those of ordinary skill in the art through consideration of the following Detailed Description and the accompanying drawings.

BRIEF DESCRIPTION OF THE DRAWINGS

The drawings illustrate several embodiments of the invention, wherein identical reference numerals refer to identical or similar elements or features in different views or embodiments shown in the drawings.

FIG. 2A shows RGC immunostaining and FIG. 2B shows the quantitative effects on RGC numbers.

FIG. 3A shows RGC immunostaining and FIG. 3B shows the quantitative effects on RGC numbers.

FIG. 4A shows Brn3a-positive RGC immunostaining, FIG. 4B shows Brn3a-positive RGC counts, and FIG. 4C shows the percentage of Brn3a-positive RGC cells remaining.

FIG. 6A shows RBPMS-positive RGC immunostaining, FIG. 6B shows RBPMS-positive RGC counts, and FIG. 6C shows the percentage of RBPMS-positive RGC cells remaining.

FIG. 8A shows RGC immunostaining and FIG. 8B shows the quantitative effects on RGC numbers.

DETAILED DESCRIPTION

Figure 1:
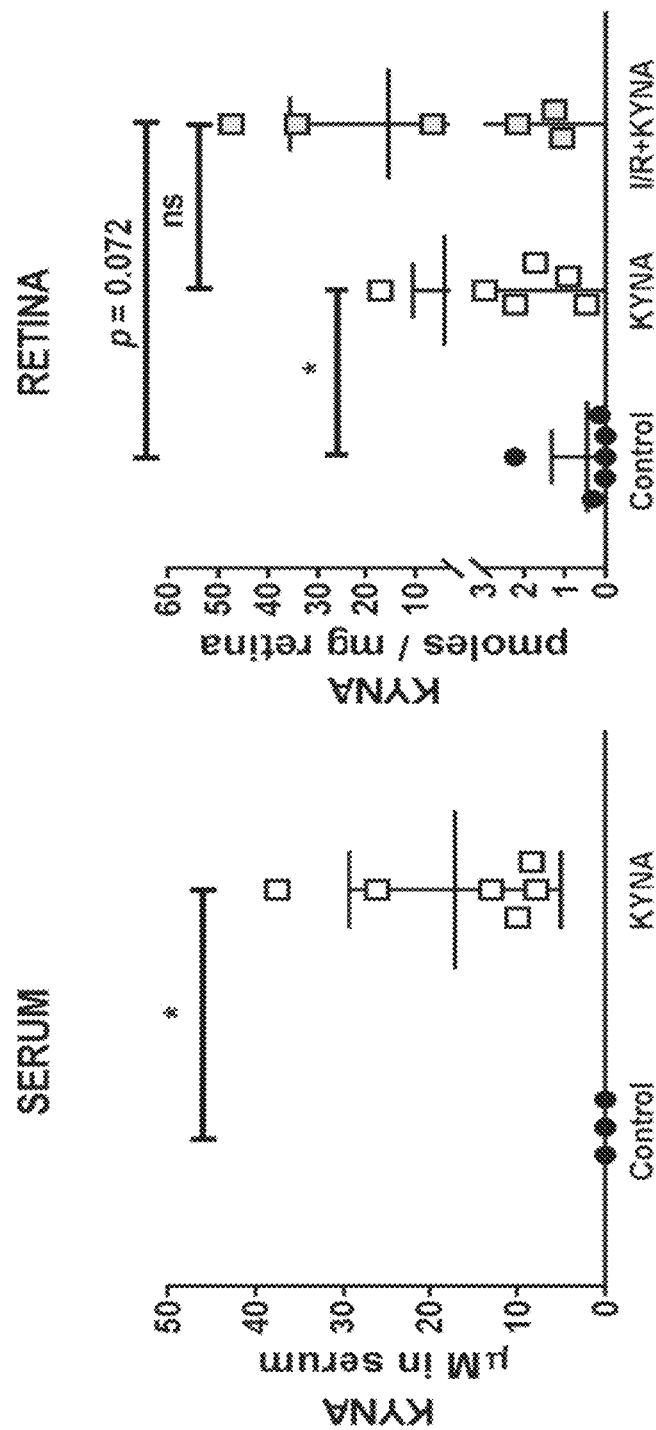
FIG. 1 shows kynurenic acid levels measured in serum and retinal samples extracted from mice intravenously injected with kynurenic acid according to an embodiment.

This disclosure relates to methods and systems of treating, reducing the risk of, preventing, or alleviating at least one symptom of retinal damage caused by glaucoma or other factors. Methods of treating retinal damage disclosed herein involve reducing or preventing RGC death via intravenous or intravitreal administration of exogenous kynurenic acid. The kynurenic acid can be administered one or more times after a subject is diagnosed with an ophthalmologic condition, such as glaucoma, or after a subject sustains an eye injury. Administration of kynurenic acid in the manner disclosed, which may increase retinal kynurenic acid levels, can cause a significant decrease in RGC death that would otherwise occur after the injury or onset of the ophthalmologic condition. The particular dose of kynurenic acid may vary and may depend on the route of administration, among other factors.

Treating retinal damage, as contemplated herein, encompasses treating, reducing the risk of, preventing, or alleviating at least one symptom of retinal damage caused by a disease, injury, or other condition. Accordingly, "treating" or "treatment" or "alleviation" refers to both therapeutic treatment and prophylactic or preventative measures, wherein the object is to prevent or slow down (lessen) the targeted pathological condition, disorder and/or symptom. Those in need of treatment include those already with the condition as well as those prone to have the condition or those in whom the condition is to be prevented. A subject is successfully "treated" for retinal damage if, after receiving a therapeutic amount of kynurenic acid according to methods of this disclosure, the subject shows observable and/or measurable reduction in, or absence of, one or more of eyesight loss, eyesight abnormalities, and RGC death. The terms "treat" or "treating" are used consistently herein for ease of illustration, only, and thus should not be construed as limiting.

An "effective amount" of kynurenic acid is an amount sufficient to carry out a specifically stated purpose. An "effective amount" may be determined empirically and in a routine manner, in relation to the stated purpose. The term "therapeutically effective amount" refers to an amount of kynurenic acid to "treat" a disease, injury, or other condition in a subject.

As used herein, "subject" means a human or other mammal. Preferably, the subject is a human. Non-human subjects may include, but are not limited to, various mammals including domestic pets and/or livestock, for example. A subject can be considered in need of treatment. The disclosed methods and systems may be effective to treat healthy human subjects, patients diagnosed with glaucoma, patients diagnosed with one or more other ophthalmologic diseases, patients suffering from various eye injuries, diabetic patients, or patients experiencing loss of eyesight.

"Reducing," "reduce," or "reduction" means decreasing the severity, scope, frequency, or length of retinal damage.

"Administration of" and "administering a" compound, composition, or agent should be understood to mean providing a compound, composition, or agent, a prodrug of a compound, composition, or agent, or a pharmaceutical composition as described herein. The compound, agent or composition can be provided or administered by another person to the subject (e.g., intravenously or intravitreally) or it can be self-administered by the subject (e.g., as an eye droplet).

"Pharmaceutical compositions" or "pharmaceutical formulations" are compositions that include an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's Pharmaceutical Sciences, Mack Publishing Co., Easton, Pa. (19th Edition).

As used herein, a "pharmaceutically-acceptable excipient" or a "pharmaceutically-acceptable carrier" means a pharmaceutically acceptable material, composition, or vehicle involved in giving form or consistency to the pharmaceutical composition. Each excipient or carrier must be compatible with other ingredients of the pharmaceutical composition when comingled such that interactions which would substantially reduce the efficacy of the kynurenic acid compositions of this disclosure when administered to a subject and interactions which would result in pharmaceutical compositions that are not pharmaceutically acceptable are avoided. In addition, each excipient or carrier must be of sufficiently high purity to render it pharmaceutically acceptable.

Prodrugs of the disclosed kynurenic acid formulations also are contemplated herein. A prodrug is an active or inactive compound that is modified chemically through in vivo physiological action, such as hydrolysis, metabolism and the like, into an active compound following administration of the prodrug to a subject. The term "prodrug" as used throughout this disclosure means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability and are readily metabolized into the active agents in vivo. Prodrugs of compounds described herein may be prepared by modifying functional groups present in the compounds in such a way that the modifications are cleaved, either by routine manipulation or in vivo, to the parent compound. The suitability and techniques involved in making and using prodrugs are well known by those skilled in the art. For a general discussion of prodrugs involving esters see Svensson and Tunek, Drug Metabolism Reviews 165 (1988) and Bundgaard, Design of Prodrugs, Elsevier (1985).

The singular terms "a," "an," and "the" include plural referents unless context clearly indicates otherwise. Similarly, the word "or" is intended to include "and" unless the context clearly indicates otherwise. The term "comprises" means "includes." Also, "comprising A or B" means including A or B, or A and B, unless the context clearly indicates otherwise. It is to be further understood that all molecular weight or molecular mass values given for compounds are approximate, and are provided for description. Although methods and materials similar or equivalent to those described herein can be used in the practice or testing of this disclosure, suitable methods and materials are described below. In addition, the materials, methods, and examples are illustrative only and not intended to be limiting.

Unless otherwise defined, all technical and scientific terms used herein have the same meaning as commonly understood by one of ordinary skill in the art to which this disclosure belongs. In the case of conflict, the present specification, including definitions, will control. All publications, patent applications, patents, and other references mentioned herein are incorporated by reference. The references cited herein are not admitted to be prior art to the claimed invention.

Therapeutic Methods

The formulations containing kynurenic acid described herein are suitable for the treatment of, reduction in the risk of, prevention of, or alleviation of at least one symptom of a variety of ophthalmologic diseases, injuries, or other conditions. Ophthalmologic diseases, injuries or conditions are those that negatively affect one or both eyes of a subject. Ophthalmologic diseases, injuries, and conditions targeted by the therapeutic methods disclosed herein may damage retinal tissue specifically.

Without intending to be bound by theory, kynurenic acid may be neuroprotective in the retina. Consistent with this theory, retinal kynurenic acid production may increase with decreased expression of kynurenine 3-monooxygeniase (KMO), which is an enzyme in the kynurenine pathway (KP) that produces neurotoxic 3-hydroxykynurenine. Decreased KMO expression may also inhibit injury-mediated RGC loss, and thus inhibition of KMO may constitute an alternative or supplemental strategy for reducing RGC death caused by various ophthalmologic diseases, injuries, or conditions.

Kynurenic acid administration may effectively protect neuronal cells damaged in several retinal degenerative diseases or injuries. Accordingly, the pharmaceutical formulations of this disclosure are suitable for treating, reducing the risk of, preventing, or alleviating at least one symptom of ophthalmologic diseases, injuries, or conditions caused by or associated with glaucoma, macular degeneration, diabetic eye disease, retinal detachment, retinitis pigmentosa, excitotoxic damage, physical damage, e.g., ischemia and/or reperfusion, chemical damage, neurotrophic factor deprivation, oxidative stress, inflammation, mitochondrial dysfunction, axonal transport failure, or combinations thereof.

In various embodiments, the pharmaceutical formulations of this disclosure are suitable for treating, reducing the risk of, preventing, or alleviating at least one symptom of ophthalmologic diseases, injuries, or conditions caused by or associated with RGC death. RGC death may be caused by or associated with various diseases, including glaucoma.

The formulations of this disclosure can be administered to a subject before or after an ophthalmologic injury or onset of a disease. Typically, the formulations of this disclosure are administered to a subject after an ophthalmologic injury or disease diagnosis. For example, formulations may be administered immediately following an injury, such as within one, two, six, 12 or 24 hours after an injury. The formulations may be administered once or multiple times, for example two, three, four, five, six, seven, eight, nine, ten times, or more. In specific embodiments, a kynurenic acid formulation is administered immediately, e.g., less than one hour, after an injury, and again at about 24 hours post-injury.

The frequency of kynurenic acid administration may vary. In embodiments, an effective amount of kynurenic acid may be administered once daily for the duration of a treatment period. Embodiments may also involve twice-daily administrations of kynurenic acid, or doses administered on a weekly basis, for example one, two, three, four, five, six or more times per week. Monthly administrations may also be implemented, such that kynurenic acid formulations are administered one, two, three, four, or more times per month.

The number of times the disclosed formulations are administered to a subject, along with the length of the treatment period, may depend on the severity or type of condition causing, or at risk of causing, retinal damage. For example, embodiments in which kynurenic acid is administered to treat an eye injury may involve fewer discrete administrations than embodiments in which kynurenic acid is administered to treat a disease, such as glaucoma, which may require a more sustained treatment approach. Accordingly, the treatment period for treating an eye injury may be about one week or less, e.g., between about one and six days, while the treatment period for treating an ophthalmologic disease or condition may be about one week or more, e.g., between about one week and one month, or longer. The length of the treatment period may also be patient-specific and re-evaluated periodically by a physician or other health care provider.

Pharmaceutical Formulations

Kynurenic acid compositions of this disclosure may be administered as a pharmaceutical formulation. Kynurenic acid of this disclosure may be formulated into a dosage form adapted for intravenous, intravitreal, or topical administration to a subject. Intra-arterial, subcutaneous, or intraperitoneal injection may also be used. Dosages may be provided initially in liquid form or as a dry powder, which may be subsequently dissolved in a liquid before administration to the subject.

In embodiments, the kynurenic acid may be administered concurrently with one or more excipients. Suitable excipients may vary depending upon the particular dosage chosen. In addition, suitable pharmaceutically acceptable excipients may be chosen for a particular function that they may serve in the formulation. Alternatively or additionally, certain pharmaceutically acceptable excipients may be chosen for their ability to facilitate the production of stable dosage forms. Alternatively or additionally, certain pharmaceutically acceptable excipients may be chosen for their ability to enhance compliance.

In embodiments, the kynurenic acid may be administered concurrently with one or more buffering agents and/or diluents. Non-limiting examples include sodium hydroxide and sodium phosphate, the concentrations of which may vary. For example, formulations herein may include kynurenic acid mixed with 0.1 M sodium hydroxide, diluted in 0.1 M sodium phosphate buffer.

Additional excipients that may be used include the following: fillers, binders, disintegrants, lubricants, glidants, granulating agents, coating agents, wetting agents, solvents, co-solvents, suspending agents, emulsifiers, coloring agents, anticaking agents, humectants, chelating agents, plasticizers, viscosity agents, antioxidants, preservatives, stabilizers, and surfactants. The skilled artisan will appreciate that certain pharmaceutically acceptable excipients may serve more than one function and may serve alternative functions depending on how much of the excipient is present in the formulation and which other ingredients are present in the formulation.

The therapeutically effective concentration of kynurenic acid administered to a subject may vary. In embodiments, each intravenous dose of kynurenic acid provided to a subject in grams per kilogram of body weight may range about 0.05 g or less per kg, about 0.1 g per kg, about 0.15 g per kg, about 0.2 g per kg, about 0.25 g per kg, about 0.3 g per kg, about 0.35 g per kg, about 0.4 g per kg, about 0.45 g per kg, about 0.5 g per kg, about 0.6 g per kg, about 0.7 g per kg, about 0.8 g per kg, about 0.9 g per kg, about 1.0 g per kg, about 1.5 g per kg, about 2.0 g per kg, about 2.5 g per kg, or more, or any dose therebetween. For example, a person weighing 180 lbs receiving intravenous kynurenic acid according to embodiments herein may be administered a single dose of about 40.8 grams of kynurenic acid. (Calculation: 180 lbs=81.65 kg; 81.65 kg×0.5 g kynurenic acid per kg body weight=40.8 g kynurenic acid). Intravenous administration of kynurenic acid at the disclosed doses may be effective to cross the blood retinal barrier. Each intravitreal dose of kynurenic acid provided to a subject may be about 5 mg or less, about 6 mg, about 7 mg, about 8 mg, about 9 mg, about 10 mg, about 12 mg, about 14 mg, about 16 mg, about 18 mg, about 20 mg, about 25 mg, about 30 mg, about 35 mg, about 40 mg, about 45 mg, about 50 mg, or more, or any dose therebetween. The dosage unit involved depends, for example, on the particular condition treated, nature of the formulation, nature of the condition, embodiment of the claimed pharmaceutical compositions, mode of administration, and condition and weight of the patient. Dosage levels are typically sufficient to achieve a tissue concentration at the site of action that is at least the same as a concentration that has been shown to be active in vitro, in vivo, or in tissue culture.

The kynurenic acid may be administered using an injection device, such as an IV drip device, infusion pump, and/or tuberculin syringe. An injection device may form part of a system for treating, reducing the risk of, preventing, or alleviating at least one symptom of retinal damage.

Kynurenic acid may also be provided as a topical composition, for example in droplet form. Drops, such as eye drops (ophthalmological compositions), may be formulated with an aqueous or non-aqueous base also comprising one or more dispersing agents, solubilizing agents or suspending agents. Liquid sprays are delivered from pressurized packs. Drops can be delivered by means of a simple eye dropper-capped bottle or by means of a plastic bottle adapted to deliver liquid contents dropwise by means of a specially shaped closure. According to such embodiments, the concentration of kynurenic acid administered may be greater than the concentrations utilized for intravenous and/or intravitreal implementations.

The following Examples are illustrative and should not be interpreted in any way as to limit the scope of the claimed invention.

EXAMPLES

Example 1

To evaluate the effects of kynurenic acid on retinal conditions characterized by RGC death, e.g., glaucoma, wild-type (WT) mice were subjected to ischemia/reperfusion (I/R) injury, which induced RGC death. I/R injury was performed by first anesthetizing 12-week-old WT (C57BL/6J) mice with an intraperitoneal injection of ketamine/xylazine confirmed by the toe-pinch test. The mice were then placed on a heating pad throughout the procedure to maintain their body temperature. The right eye of each animal was cannulated into the anterior chamber with a 33-gauge needle connected to an elevated saline reservoir. The height of the reservoir was adjusted to achieve an intraocular pressure of 120 mmHg. After 60 min of this procedure, the needle was removed.

Treatment mice were given kynurenic acid intravenously or intravitreally, while control mice were subjected to the same I/R injury but not given kynurenic acid. Intravenous and intravitreal administration of kynurenic acid was performed immediately after I/R injury and again 24 hours post-injury. Kynurenic acid was injected intravenously via the tail vein into WT mice at a concentration of 2.5 mg/animal (25 mg/mL stock dissolved in 0.1 N NaOH, diluted in 0.1 M sodium phosphate buffer, and adjusted to pH 7). After 2 hours, kynurenic acid levels in the serum and retina were measured. Control animals received 0.1 M sodium phosphate buffer (pH 7) alone.

Kynurenic acid was injected intravitreally into separate WT mice at a concentration of either 5 or 10 μg/animal (5 mg/mL stock of kynurenic acid was dissolved in 0.1 N NaOH and diluted in 0.1 M sodium phosphate buffer adjusted to pH 7). Control animals were intravitreally injected with buffer alone. Intravitreal injection was performed using a 33-gauge needle attached to a Hamilton syringe (Hamilton Bonaduz AG, Bonaduz, Switzerland). The eye lids were carefully parted, and the 33-gauge needle was inserted at a 45° angle into the vitreous, just behind the limbus. One or two microliters of solution was injected in 1 μL increments with a 30 second gap between each injection. After injection, the needle was slowly withdrawn, and the injected area was treated with a topical antibiotic. Mice were anesthetized with a cocktail containing ketamine and xylazine prior to the intravitreal injections.

All mice were euthanized and retinas dissected 14 days after I/R injury, flat-mounted and immunostained for Brn3a (brain-specific homeobox/POU domain protein 3A), which is a marker for RGCs.

To first determine whether kynurenic acid is permeable across the blood retinal barrier, kynurenic acid levels in the serum and retina of six WT mice intravenously injected with kynurenic acid (KYNA) were measured by LC=MS/MS two hours after injection. As shown in FIG. 1, kynurenic acid levels increased significantly (*$p<0.05$; ns=not significant) in serum and retinal samples from kynurenic acid-injected mice relative to sodium phosphate buffer-injected control mice. Similar increases in retinal samples from kynurenic acid-injected mice subjected to I/R injury were also measured. These data indicate that kynurenic acid may exhibit at least some permeability across the blood retinal barrier.

Figure 2A:
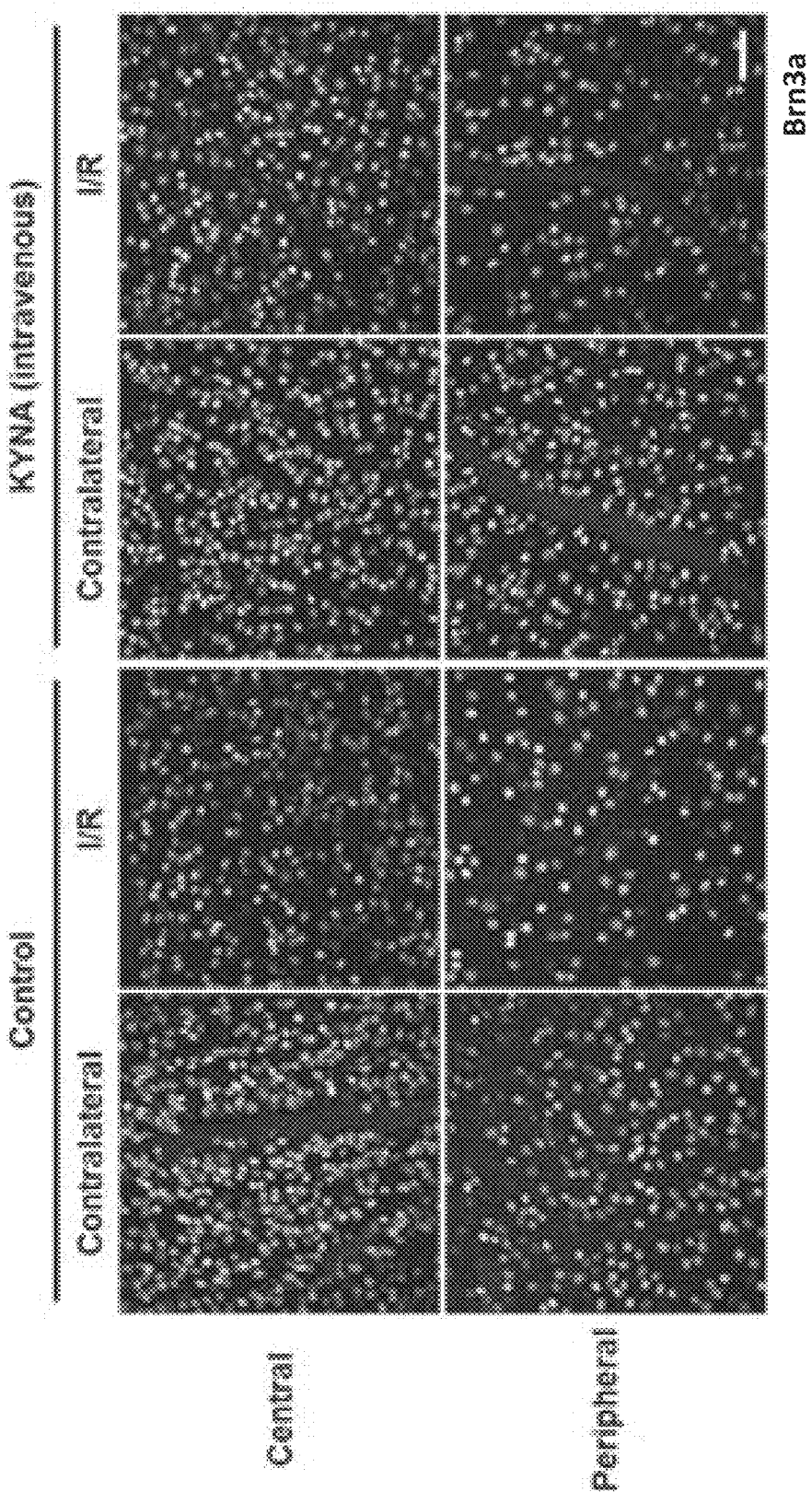
FIGS. 2A and 2B show the effects of intravenous administration of kynurenic acid on the central and peripheral retinas in injured and non-injured mice according to an embodiment.
Figure 2B:
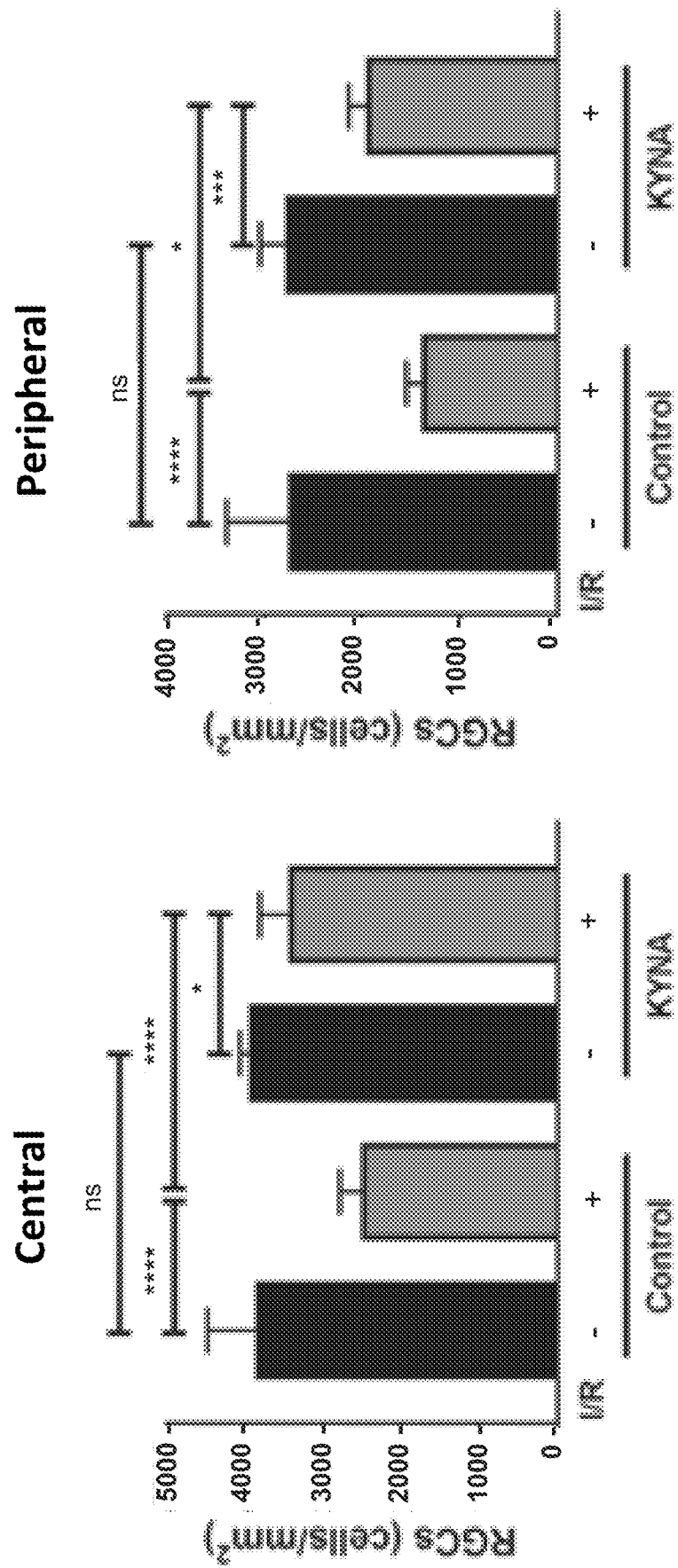

The effects of administration of kynurenic acid on RGC loss in the central and peripheral retina are shown in FIGS. 2A, 2B, 3A, and 3B, in which ns=not significant, *p<0.05, p<0.01, *p<0.001, ****p<0.0001, and scale bar=50 μm. As shown in FIG. 2A, WT mice given kynurenic acid (n=5) intravenously exhibited reduced RGC loss compared to WT mice not given kynurenic acid (n=5), as evidenced by greater Brn3a-positive RGC staining in the injured mice administered kynurenic acid. As evidenced by the number of RGCs present per square millimeter, shown graphically in FIG. 2B, the level of RGC loss was 36.3% and 50% in the central and peripheral retina, respectively, of mice subjected to I/R injury, but only 11.2% and 29.4% in mice subjected to I/R injury but also administered kynurenic acid. The protective effect of kynurenic acid thus appears more pronounced in the central retina than the peripheral retina in mice treated intravenously with kynurenic acid.

Figure 3A:
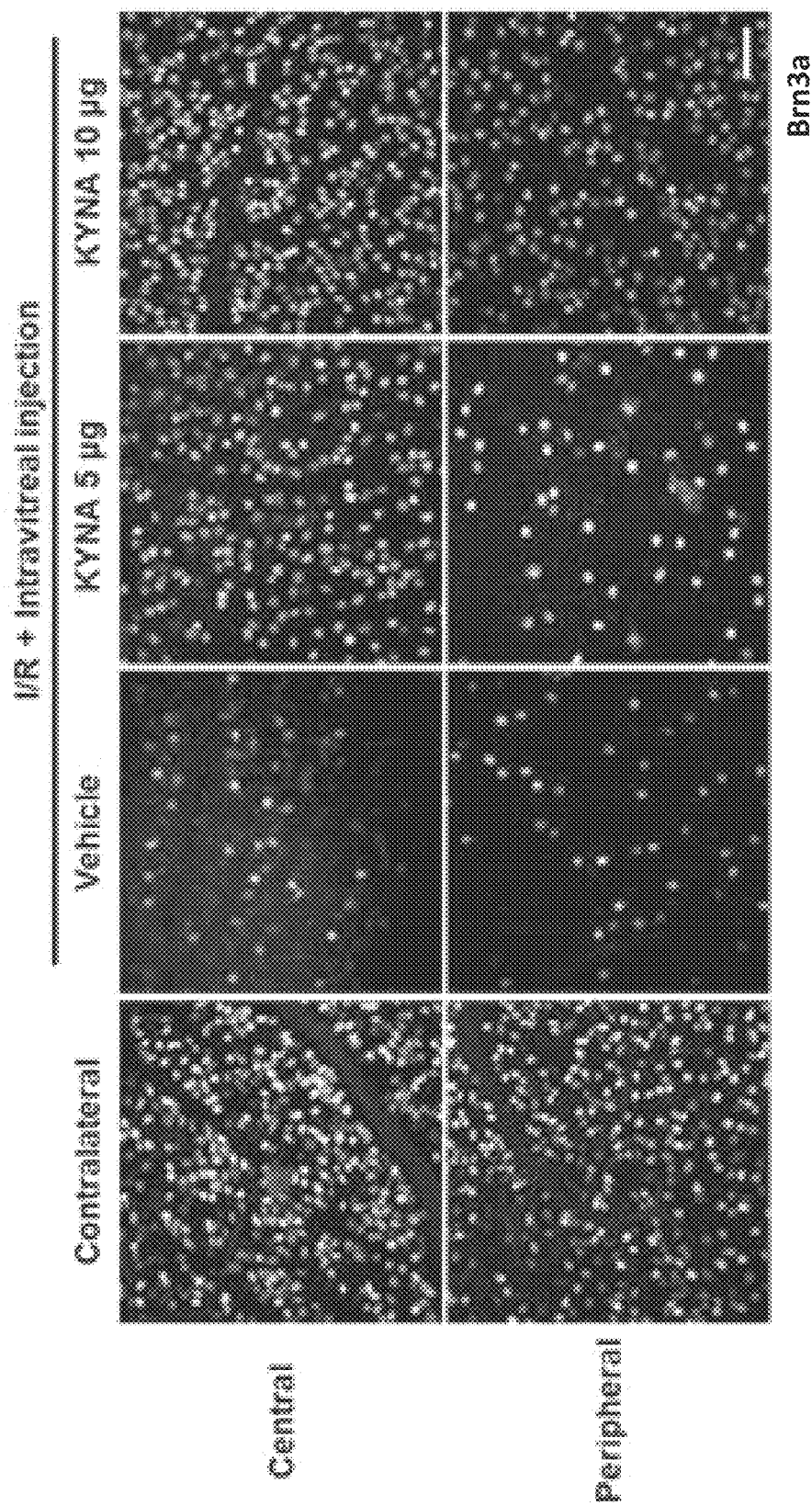
FIGS. 3A and 3B show the effects of intravitreal administration of kynurenic acid at multiple doses on the central and peripheral retinas in injured and non-injured mice according to an embodiment.
Figure 3B:
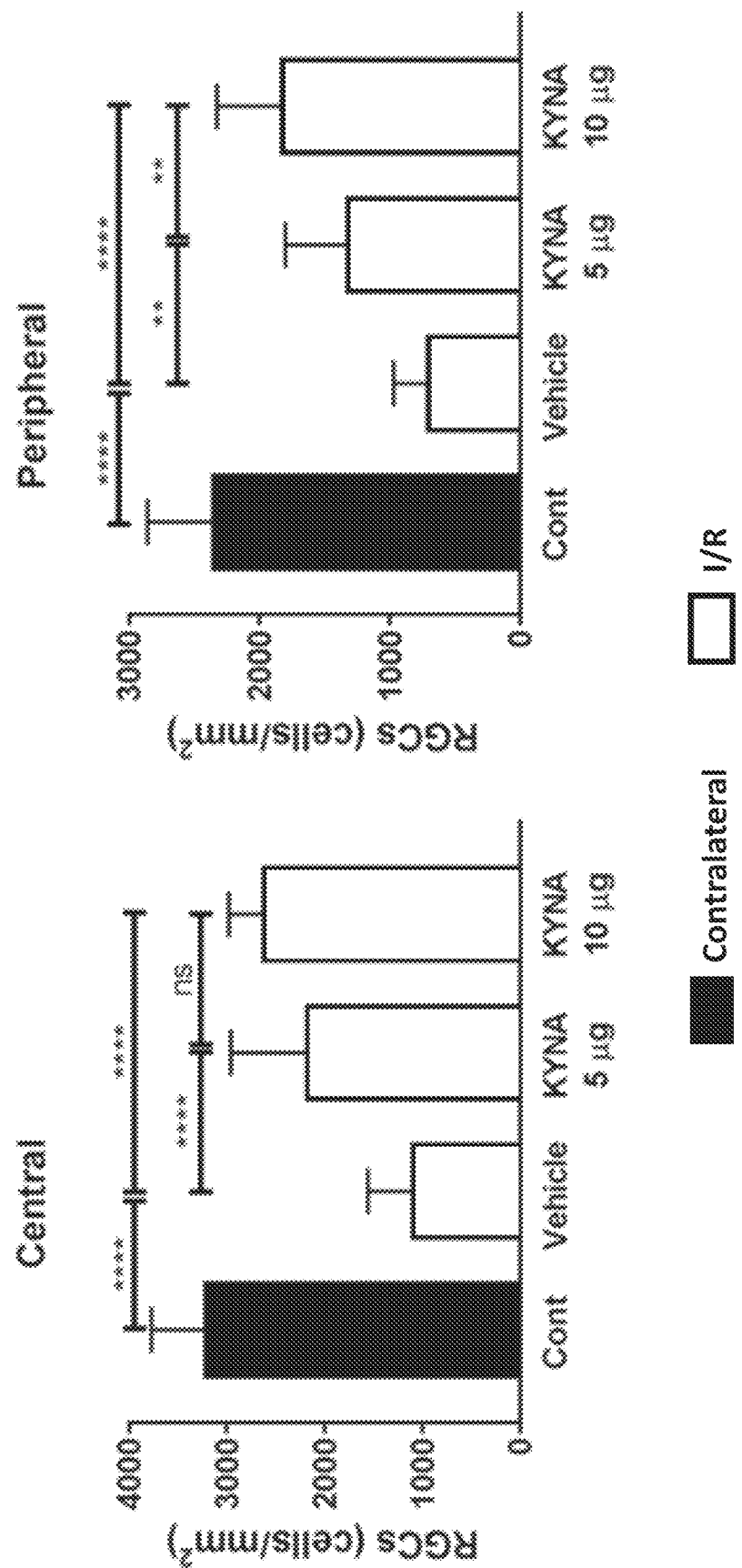

FIGS. 3A and 3B show the effects of intravitreal administration of kynurenic acid on RGC loss in the central and peripheral retina. Kynurenic acid was administered at three doses: 0 μg (control), 5 μg (n=8), and 10 μg (n=7). As shown in FIG. 3A, WT mice given 10 μg kynurenic acid intravitreally exhibited greater reduction in Brn3a-positive RGC loss compared to WT mice given 5 μg kynurenic acid intravitreally, and especially compared to the negative control mice not given any kynurenic acid. In particular, as shown graphically in FIG. 3B, the level of RGC loss was 66.1% and 70.9% in the central and peripheral retina, respectively, of mice subjected to I/R injury, but only 32.4% and 46.1% in the central and peripheral retina, respectively, of mice subjected to I/R injury and given 5 μg kynurenic acid intravitreally, and only 18.5% and 26.8% in mice subjected to I/R injury but also administered 10 μg kynurenic acid. The protective effect of intravitreally administered kynurenic acid thus also appears more pronounced in the central retina than the peripheral retina.

The results of Example 1 thus show that exogenous kynurenic acid, when injected intravenously or intravitreally, inhibits RGC death in an animal model of glaucoma.

Example 2

The objective of Example 2 was to investigate the role of increased retinal de novo levels of kynurenic acid in RGC death in an acute I/R injury model in mice by developing a mouse KMO knockout (KMO KO) strain (male).

Successful knockout of the KMO gene was confirmed via PCR. Elevated levels of various serum KP metabolites, including kynurenic acid, were also measured and confirmed to be higher in the KMO knockout strain relative to WT mice. Elevated kynurenic acid levels were also measured specifically in the retina of the KMO KO mice.

Figure 4A:
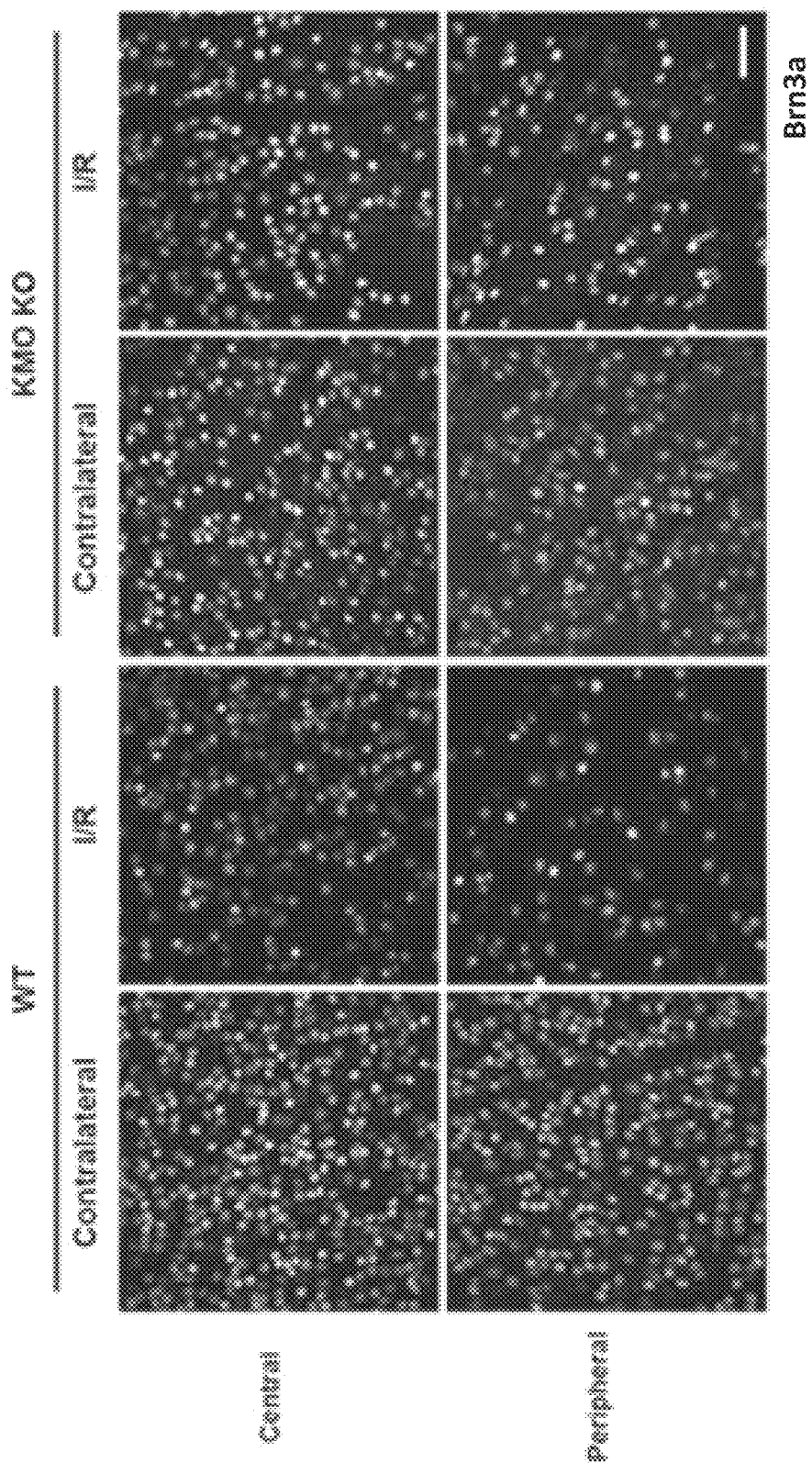
FIGS. 4A-4C show results from central and peripheral retina samples from kynurenine 3-monooxygenase knockout (KMO KO) mice and wild-type (WT) mice after injury and without injury according to an embodiment.
Figure 4B:
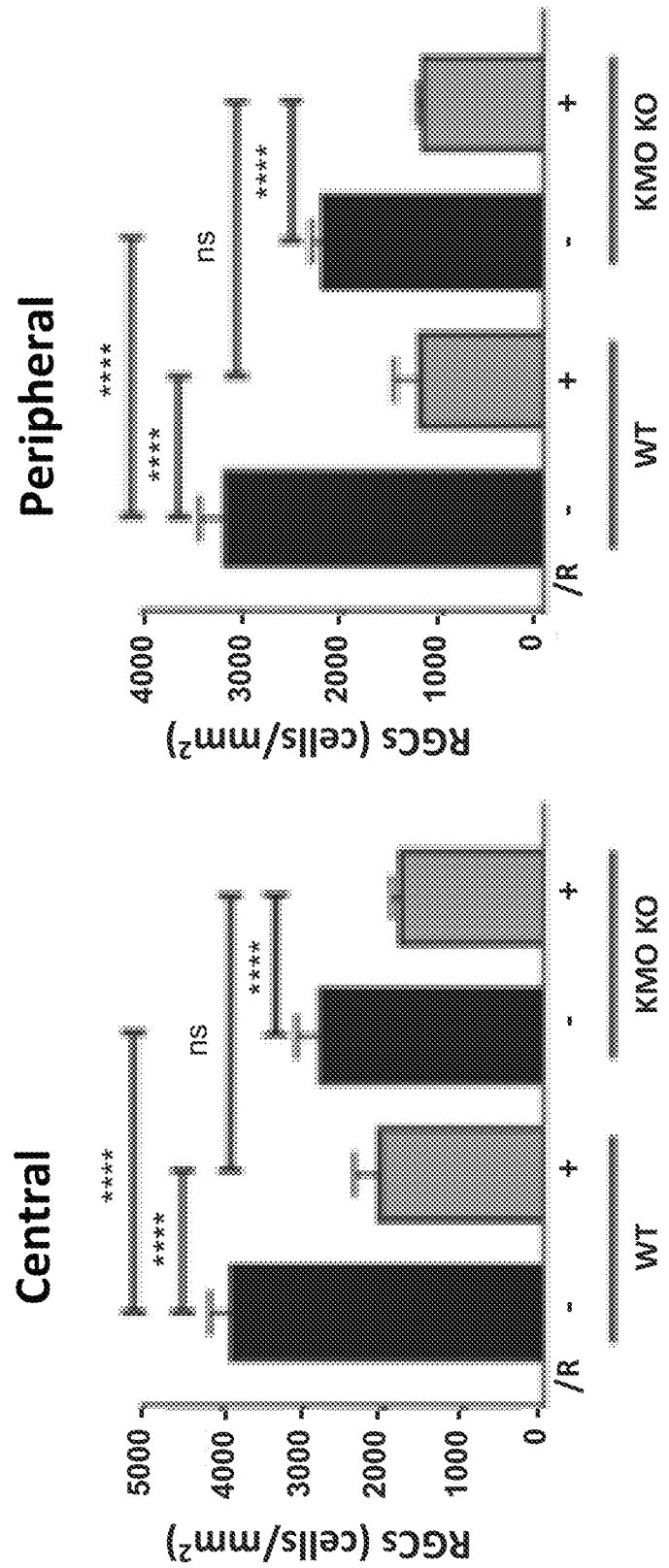
Figure 4C:
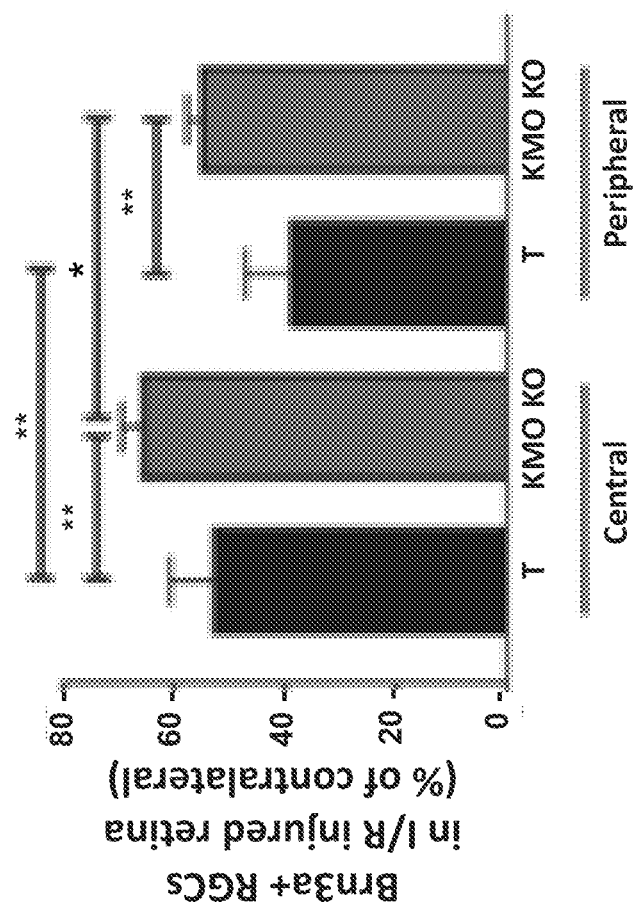
Figure 5A:
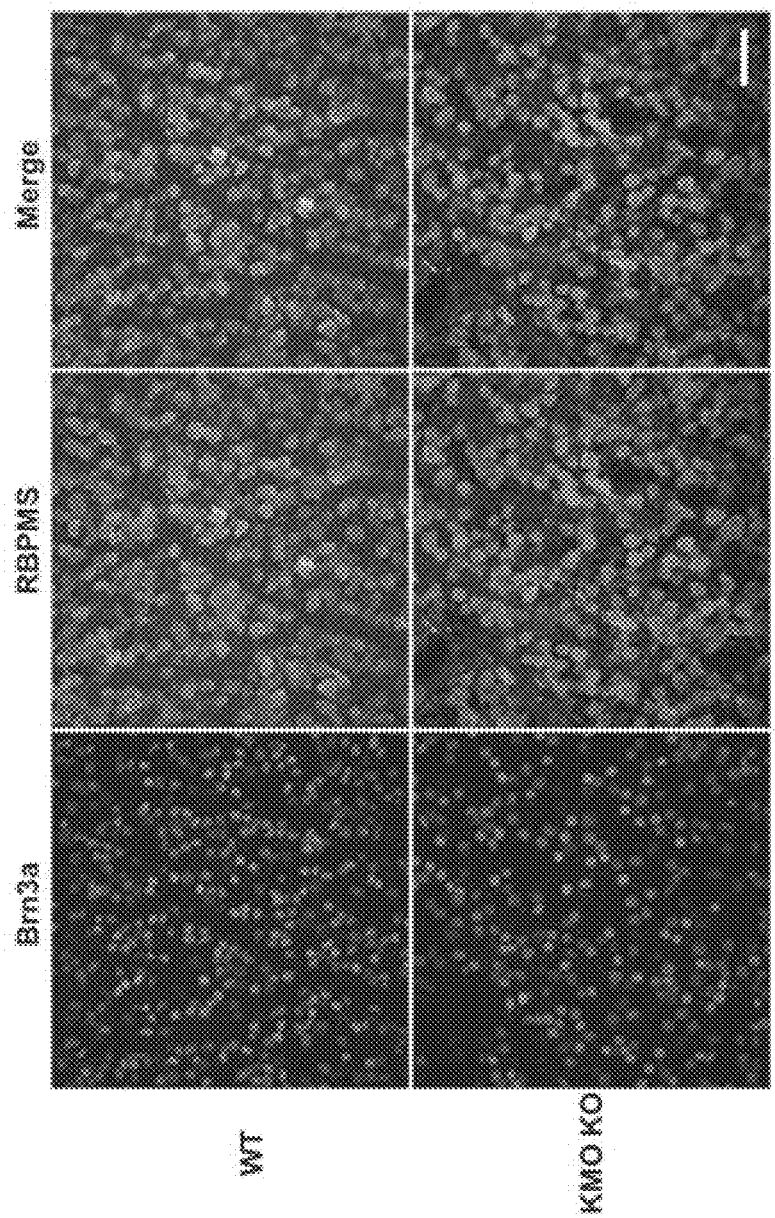
FIGS. 5A and 5B show RNA-binding protein with multiple splicing (RBPMS)-positive RGC immunostaining (5A) and RBPMS- and Brn3a-positive RGC counts (5B) from KMO KO mice and WT mice according to an embodiment.
Figure 5B:
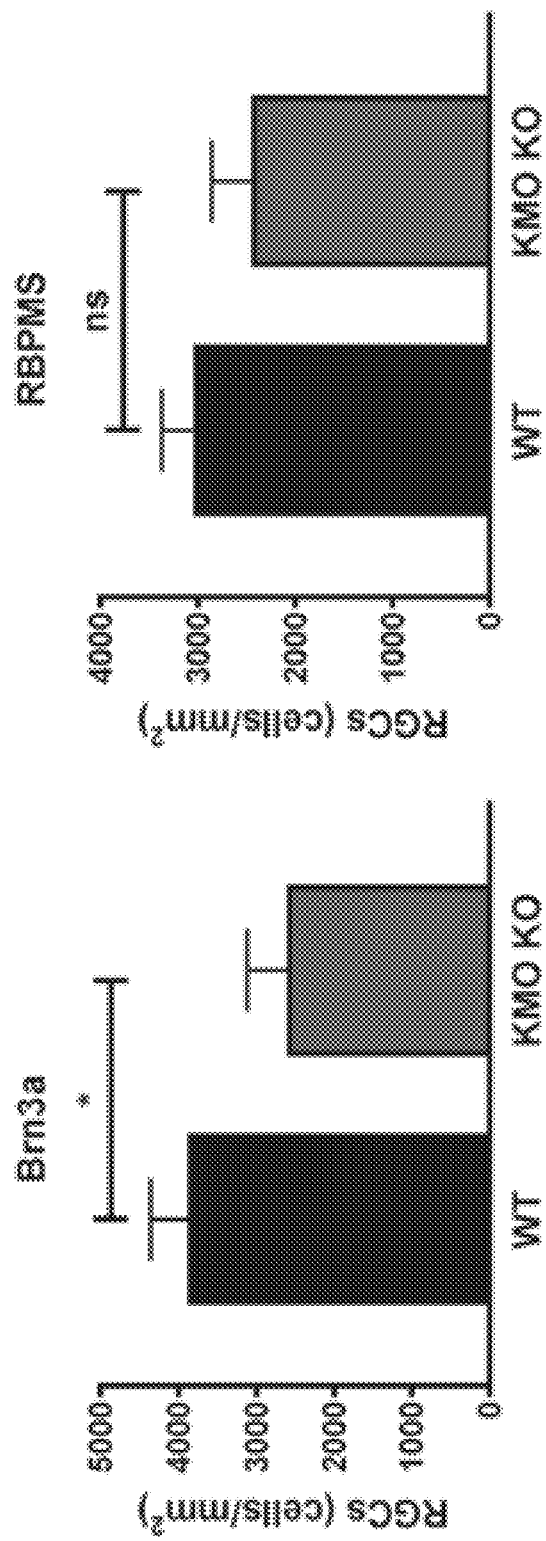
Figure 6A:
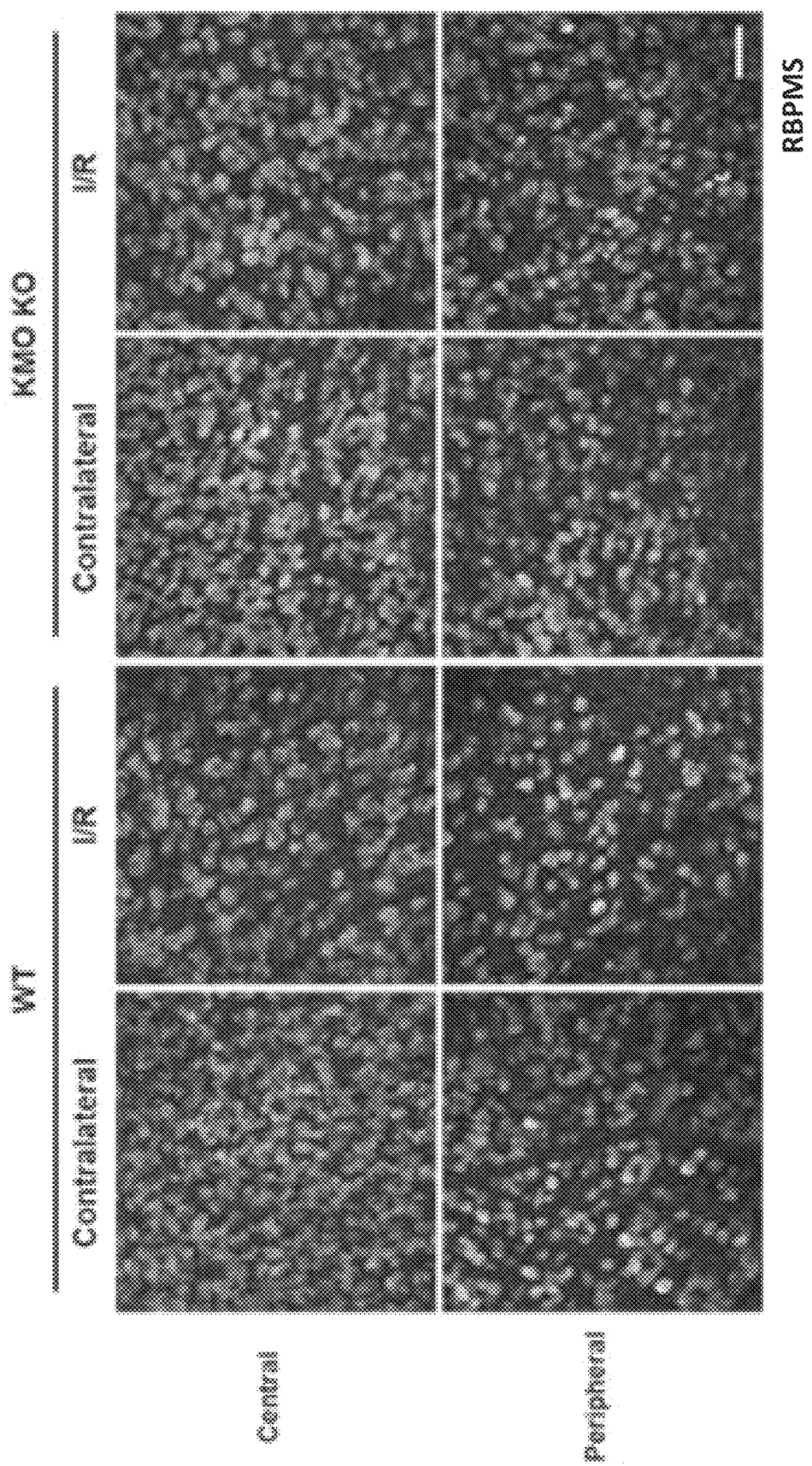
FIGS. 6A-6C show results from central and peripheral retinas of KMO KO mice and WT mice after injury and without injury according to an embodiment.
Figure 6B:
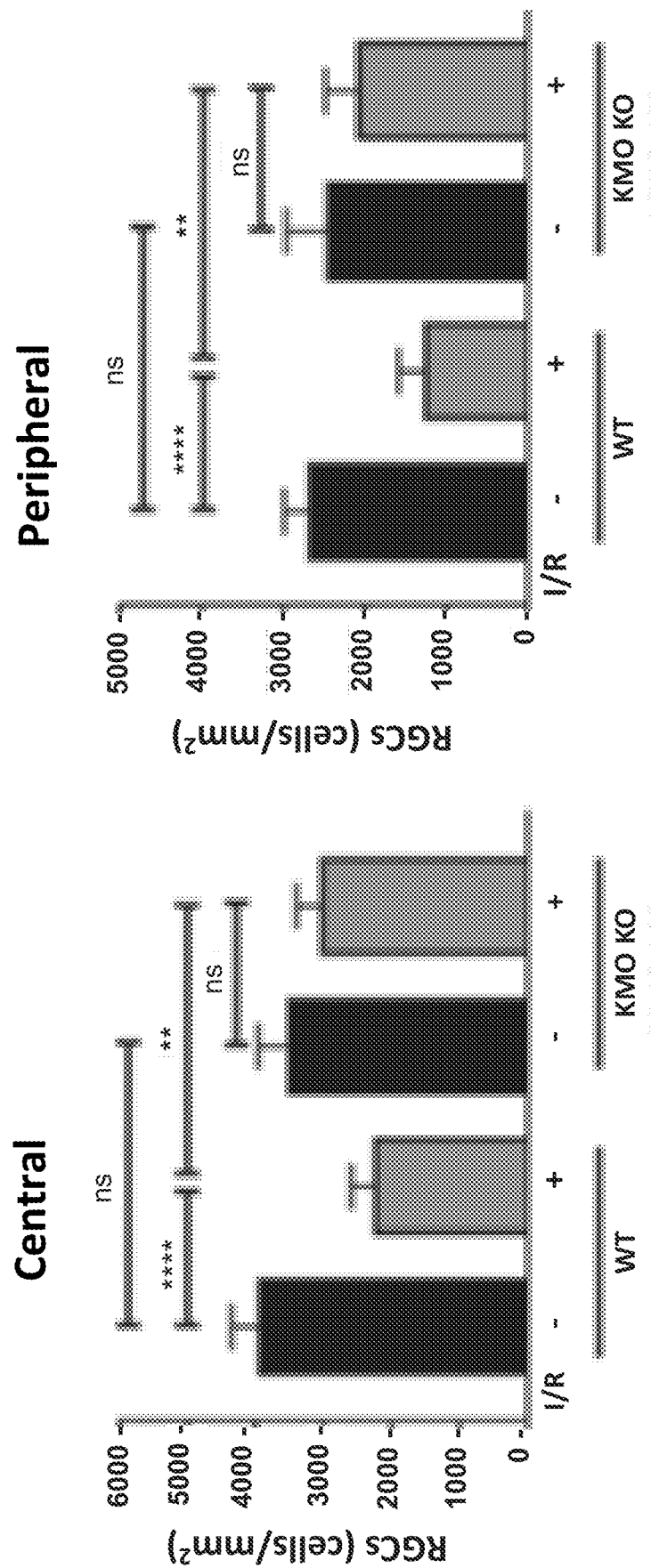
Figure 6C:
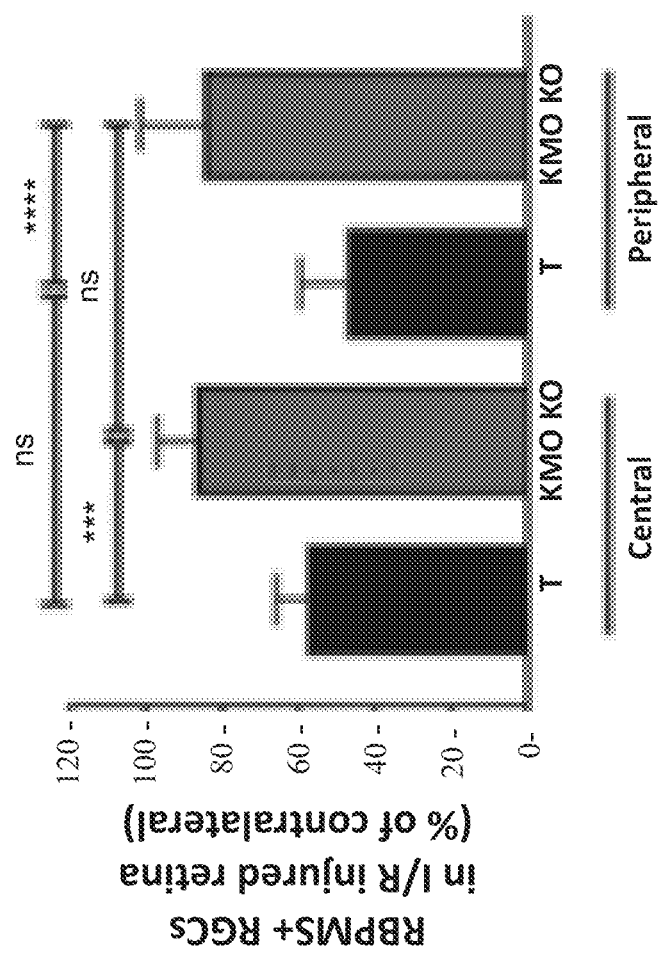

To determine whether RGCs are protected from I/R-induced damage in mice lacking KMO, WT and KMO KO mice were subjected to I/R injury in the same manner as the mice in Example 1. Results are shown in FIGS. 4A-6C, in which the bar graphs represent the means±SD of triplicate measurements, ns=not significant, *p<0.05, p<0.01, *p<0.001, ****p<0.0001, and scale bar=50 μm. As shown visually in FIG. 4A and graphically in FIG. 4B, I/R injury significantly decreased the Brn3a-positive RGC numbers both in the central and peripheral retinas from both WT (n=4) and KMO KO (n=5) mice. By contrast, FIG. 4C shows that the percentage of Brn3a-positive RGCs remained significantly higher in both the central and peripheral retinas of KMO KO mice relative to WT mice following I/R. Because there was no difference in the number of remaining RGCs after I/R between WT and KMO KO mice, dual-staining of Brn3a and RNA-binding protein with multiple splicing (RBPMS) in WT and KMO KO mouse retinas was performed. The RGC subpopulations were different between the KMO KO and WT mice, as indicated by significantly lower numbers in RBPMS-positive RGCs compared to the WT mice, as shown in FIGS. 5A and 5B. A significant reduction in RBPMS-positive RGCs in WT mice subjected to I/R injury was also observed, an effect which was less severe in the KMO KO mice (FIGS. 6A and 6B). In I/R-injured retinas, the percentage of RBPMS-positive RGCs was significantly higher in both the central and peripheral retinas of KMO KO mice relative to WT mice, as further shown in FIG. 6C.

The results of Example 2 show that the absence of KMO indeed offers protection against RGC loss induced by I/R injury.

Example 3

Figure 7:
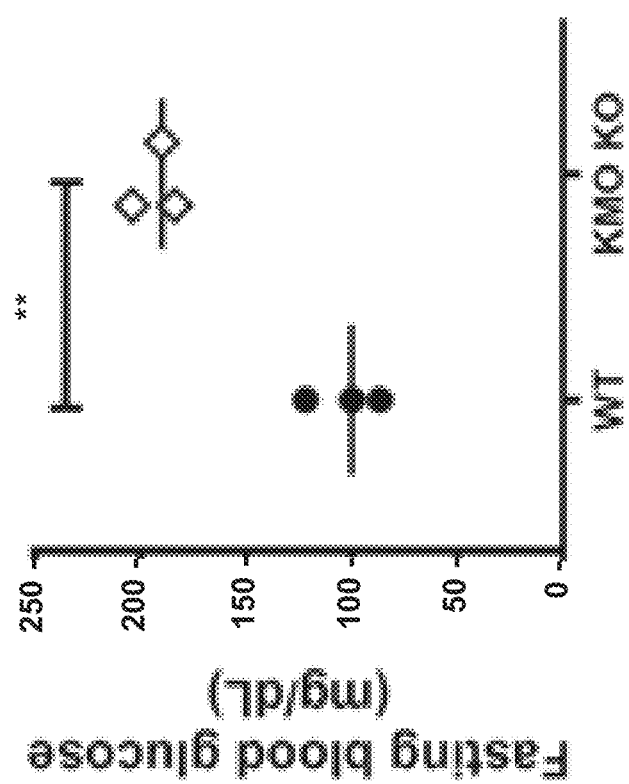
FIG. 7 shows levels of fasting blood glucose (FBG) measured in WT and KMO KO mice according to an embodiment.

Interestingly, KMO KO mice also exhibited higher levels of fasting blood glucose (FBG) than WT mice, as shown in FIG. 7. In view of this result, the objective of Example 3 was to test whether elevation of blood glucose has any effect on RGC survival against I/R injury in diabetic mice.

Figure 8A:
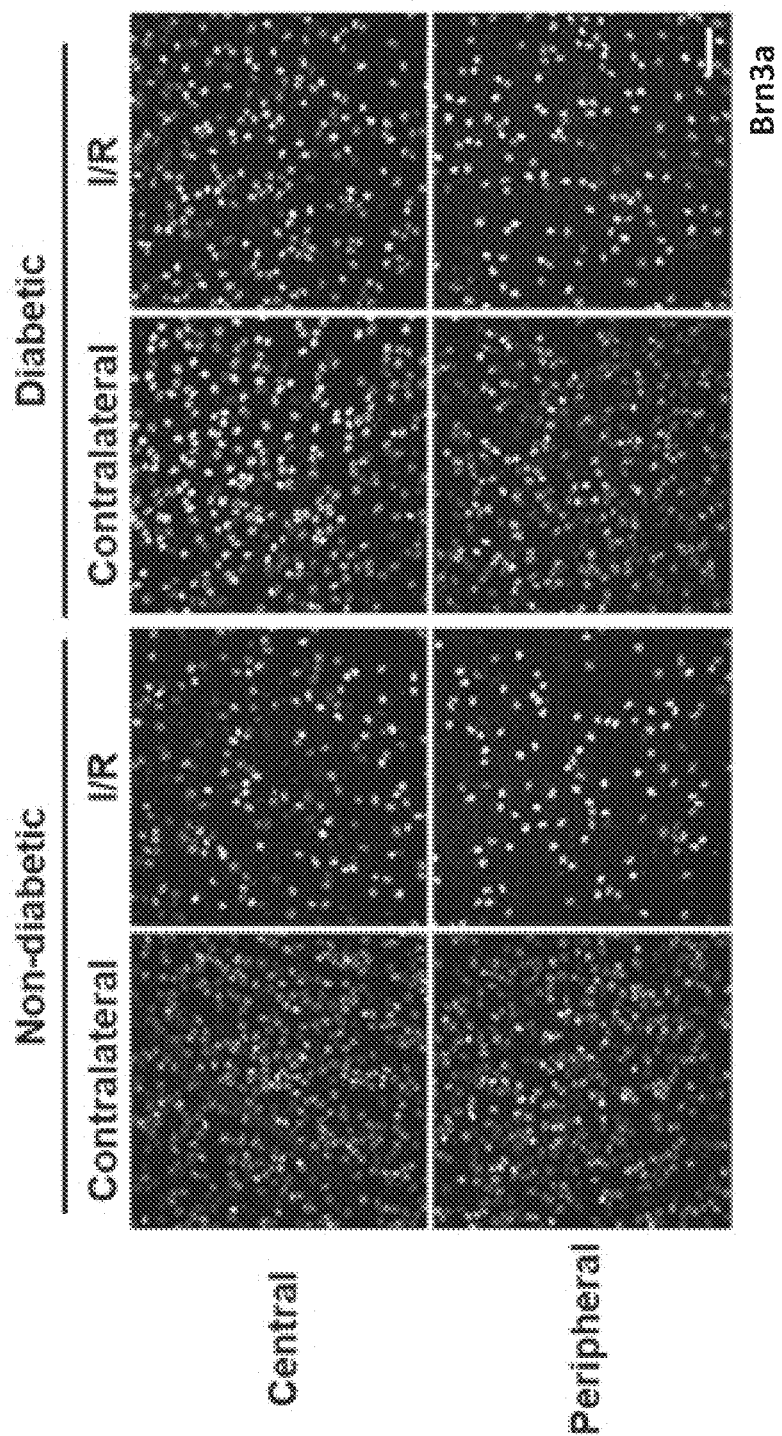
FIGS. 8A and 8B show the effects of diabetes on the central and peripheral retinas in injured and non-injured mice according to an embodiment.
Figure 8B:
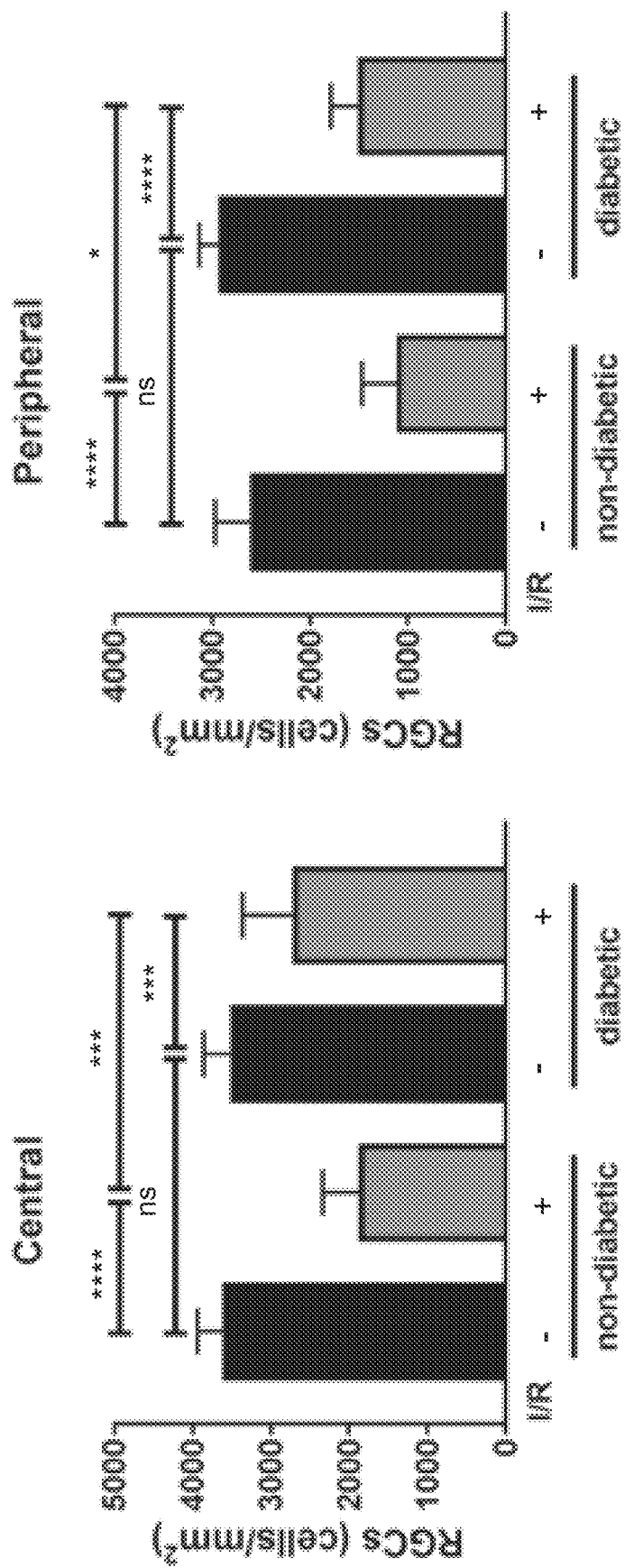

Diabetes was induced in mice via intraperitoneal injection of streptozotocin (STZ), and it was confirmed that the levels of FBG were indeed higher in the STZ-injected mice (231 mg/dl) compared to age-matched non-diabetic mice (109 mg/dl). FIGS. 8A and 8B show the effects of diabetes on RGC loss in the central and peripheral retina, in which ns=not significant, *p<0.05, *p<0.001, **p<0.0001, and scale bar=50 μm. As shown in FIG. 8A, greater Brn3a-positive RGC staining was observed in diabetic mice subjected to I/R injury compared to non-diabetic mice subjected to I/R injury, indicating that RGC loss is reduced in diabetic mice after I/R injury compared to non-diabetic mice subjected to the same injury. The graphical results shown in FIG. 8B confirm that in non-diabetic mice, I/R injury resulted in a significant 49% (p<0.0001) and 58% (p<0.0001) decrease in Brn3a-positive RGCs per square millimeter in the central and peripheral retina, respectively, compared to untreated contralateral eyes. By contrast, in diabetic mice subjected to I/R injury, the number of Brn3a-positive RGCs decreased by only 25% and 42% per square millimeter of the central (p<0.001) and peripheral (p<0.0001) retina when compared to uninjured contralateral eyes. Still further, short-term diabetes resulted in 24% (p<0.001) and 16% (p<0.05) more remaining RGCs in the central and peripheral retina compared to non-diabetic mice subjected to I/R injury.

The results of Example 3 indicate that RGCs are better protected from I/R injury in short-term diabetic mice than in non-diabetic mice.

Although various representative embodiments and implementations have been described above with a certain degree of particularity, those skilled in the art could make numerous alterations to the disclosed embodiments without departing from the spirit or scope of the inventive subject matter set forth in the specification and claims. In some instances, in methodologies directly or indirectly set forth herein, various steps and operations are described in one possible order of operation, but those skilled in the art will recognize that steps and operations may be rearranged, replaced, or eliminated without necessarily departing from the spirit and scope of the present disclosure. It is intended that all matter contained in the above description or shown in the accompanying drawings shall be interpreted as illustrative only and not limiting. Changes in detail or structure may be made without departing from the spirit of the disclosure as defined in the appended claims.

The invention claimed is:

1. A method of treating, reducing the risk of, preventing, or alleviating at least one symptom of a retinal disease, injury, or condition in a subject, the method comprising:
   administering to the subject a therapeutically effective amount of kynurenic acid.

2. The method of claim 1, wherein the kynurenic acid is administered intravenously.

3. The method of claim 2, wherein the kynurenic acid is administered at least once within 24 hours after the injury is sustained by the subject or the retinal disease or condition is diagnosed.

4. The method of claim 2, wherein the kynurenic acid is administered at a dose ranging from about 0.05 g per kg of body weight of the subject to about 0.6 g per kg of body weight of the subject.

5. The method of claim 2, wherein the kynurenic acid is administered at a dose ranging from about 0.1 g per kg of body weight of the subject to about 0.25 g per kg of body weight of the subject.

6. The method of claim 1, wherein the kynurenic acid is administered intravitreally.

7. The method of claim 6, wherein the kynurenic acid is administered at least once within 24 hours after the injury is sustained by the subject or the retinal disease or condition is diagnosed.

8. The method of claim 6, wherein the kynurenic acid is administered at a dose ranging from about 5 mg to about 50 mg.

9. The method of claim 6, wherein the kynurenic acid is administered at a dose ranging from about 5 mg to about 10 mg.

10. The method of claim 1, wherein the subject is a human.

11. The method of claim 1, wherein the retinal disease, injury, or condition is glaucoma.

12. The method of claim 1, wherein the retinal disease, injury, or condition is selected from the group consisting of: glaucoma, macular degeneration, diabetic eye disease, retinal detachment, and retinitis pigmentosa.

13. The method of claim 1, wherein the retinal disease, injury, or condition is caused by excitotoxic damage, physical damage, chemical damage, neurotrophic factor deprivation, oxidative stress, inflammation, mitochondrial dysfunction, axonal transport failure, or combinations thereof.

14. The method of claim 1, wherein the retinal disease, injury, or condition comprises a loss of retinal ganglion cells.

* * * * *